US006451598B1

(12) United States Patent
Goldsmith et al.

(10) Patent No.: US 6,451,598 B1
(45) Date of Patent: Sep. 17, 2002

(54) CELL FUSION ASSAYS FOR THE IDENTIFICATION OF ANTIVIRAL COMPOUNDS, AND SYSTEMS AND KITS FOR PRACTICING THE SAME

(75) Inventors: Mark A. Goldsmith, San Francisco, CA (US); Yun You, Williamsville, NY (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/779,324

(22) Filed: Feb. 7, 2001

(51) Int. Cl.[7] .............................. C12N 5/06; C12Q 1/68; C12Q 1/06; A61K 49/00
(52) U.S. Cl. ............................. 435/334; 435/6; 435/39; 424/9.2
(58) Field of Search .............................. 435/39, 6, 334; 424/9.2

(56) References Cited

PUBLICATIONS

Berger et al. (1995) "HIV envelope glycoprotein/CD4 interactions: studies using recombinant vaccinia virus vectors." In *HIV: A Practical Approach*, J. Karn ed., IRL Press, vol. 2:123–145.

Blondell et al. (Feb. 25, 2000) Abstract from 3rd Annual Conference on AIDS research in CA.

Broder et al. (1995) "Fusogenic selectivity of the envelope glycoprotein is a major determinant of human immunodeficiency virus type 1 tropism for CD4+ T–cell lines vs. primary macrophages." *Proc. Natl. Acad. Sci. USA*, vol. 92:9004–9008.

Doranz et al. (1997) "A Small–molecule Inhibitor Directed against the Chemokine Receptor CSCR4 Prevents its Use as an HIV–1 Coreceptor." *J. Exp. Med.*, vol. 186(8):1395–1400.

Moir et al. (1996) "Expression of HIV env Gene in a Human T Cell Line for a Rapid and Quantifiable Cell Fusion Assay." *AIDS Research and Human Retroviruses*, vol. 12:811–820.

Weiss et al. (1993) "Characterization of Stable Chinese Hamster Ovary Cells Expressing Wild–Type, Secreted, and Glycosylphosphatidylinositol–anchored Human Immunodeficiency Virus Type 1 Envelope Glycoprotein." *Journal of Virology*, vol. 67(12):7060–7066.

Weiss et al. (1996) "Studies of HIV–1 envelope glycoprotein–mediated fusion using a simple fluorescence assay." *AIDS*, vol. 10:241–246.

Yi et al. (1999) "Role of CXCR4 in Cell–Cell Fusion and Infection of Monocyte–Derived Macrophages by Primary Human Immunodeficiency Virus Type 1 (HIV–1) Strains: Two Distinct Mechanisms of HIV–1 Dual Tropism." *Journal of Virology*, vol. 73(9):7117–7125.

*Primary Examiner*—Hankyel T. Park
(74) *Attorney, Agent, or Firm*—Bret E. Field; Paula A. Borden; Bozicevic, Field & Francis, LLP.

(57) ABSTRACT

Cell fusion assays for identifying antiviral compounds are provided. In the cell fusion assays of the subject invention, a first cell that stably expresses on its surface an envelope protein of an enveloped virion and a second cell that stably expresses a receptor for the envelope protein on its surface are employed. The first and second cells each contain one component of a two component Tat reporter system that produces a detectable product in the presence of cell fusion. In practicing the subject screening methods, the first and second cells are first contacted with each other under cell fusion conditions in the presence of a candidate inhibitory agent. Next, the presence or absence of the detectable product is detected. Finally, the inhibitory activity of the candidate agent is derived from the presence or absence of the detectable product. Also provided are high throughput embodiments of the subject methods. In addition to the subject methods, systems and kits for performing the subject methods are provided.

16 Claims, 1 Drawing Sheet

CELL FUSION ASSAYS FOR THE IDENTIFICATION OF ANTIVIRAL COMPOUNDS, AND SYSTEMS AND KITS FOR PRACTICING THE SAME

TECHNICAL FIELD

This invention relates generally to the field of drug screening assays, more particularly to antiviral drug screening assays and specifically to cell fusion based antiviral drug screening assays.

BACKGROUND OF THE INVENTION

Cell fusion assays designed to identify viral inhibitory agents, i.e., agents that inhibit the binding of a viral glycoprotein and a target cell receptor as well as the virion-cell fusion that follows this binding event, are known in the art. In cell fusion assays, a first cell expresses a viral envelope coat protein on its surface and represents the "virion" while a second cell expresses a receptor for the viral coat protein on its surface and represents the target cell. When brought together under appropriate conditions, the first and second cells fuse via a viral coat protein/target cell receptor mediated event.

Many of the cell fusion assays currently employed are "vaccinia" based fusion assays in which the envelope protein of the virion of interest is only transiently expressed in the virion host cell. While such vaccinia based cell fusion assays have been extremely useful, they do suffer from certain disadvantages, including an unsuitability for adaptation to high throughput automated formats.

As such, there is continued interest in the identification of additional cell fusion assay protocols. Of particular interest would be the development of protocol that are adaptable to high throughput, automated formats.

Relevant Literature

Papers of interest include: Berger et al., HIV: A Practical Approach (J. Karn ed. IRL Press) Vol. 2:123–145 (1995); Blondell et al., Abstract from $3^{rd}$ Annual Conference on AIDS research in California, Feb. 25, 2000; Weiss et al., J. Virol. (1993) 67: 7060–7066; and Weiss et al., AIDS (1996) 10:241–246.

SUMMARY OF THE INVENTION

Cell fusion assays for identifying antiviral compounds, particularly enveloped virus inhibitory compounds, are provided. In the cell fusion assays of the subject invention, a first cell that stably expresses an envelope protein of an enveloped virion on its surface, i.e., the "virion cell," and a second cell that stably expresses a receptor for the envelope protein on its surface, i.e., the "target cell," are employed. The virion and target cells each contain one component of a two component reporter system, e.g., a Tat based two component reporter system, that produces a detectable signal in the presence of cell fusion. In practicing the subject screening methods, the first and second cells are contacted with each other under cell fusion conditions in the presence of a candidate inhibitory agent. Next, the presence or absence of the detectable signal is detected. Finally, the inhibitory activity of the candidate agent is derived from the presence or absence of the detectable signal. Also provided are high throughput embodiments of the subject methods. In addition to the subject methods, systems and kits for performing the subject methods are provided.

DETAILED DESCRIPTION OF THE PREFERRED EMBODIMENTS

Figure 1:
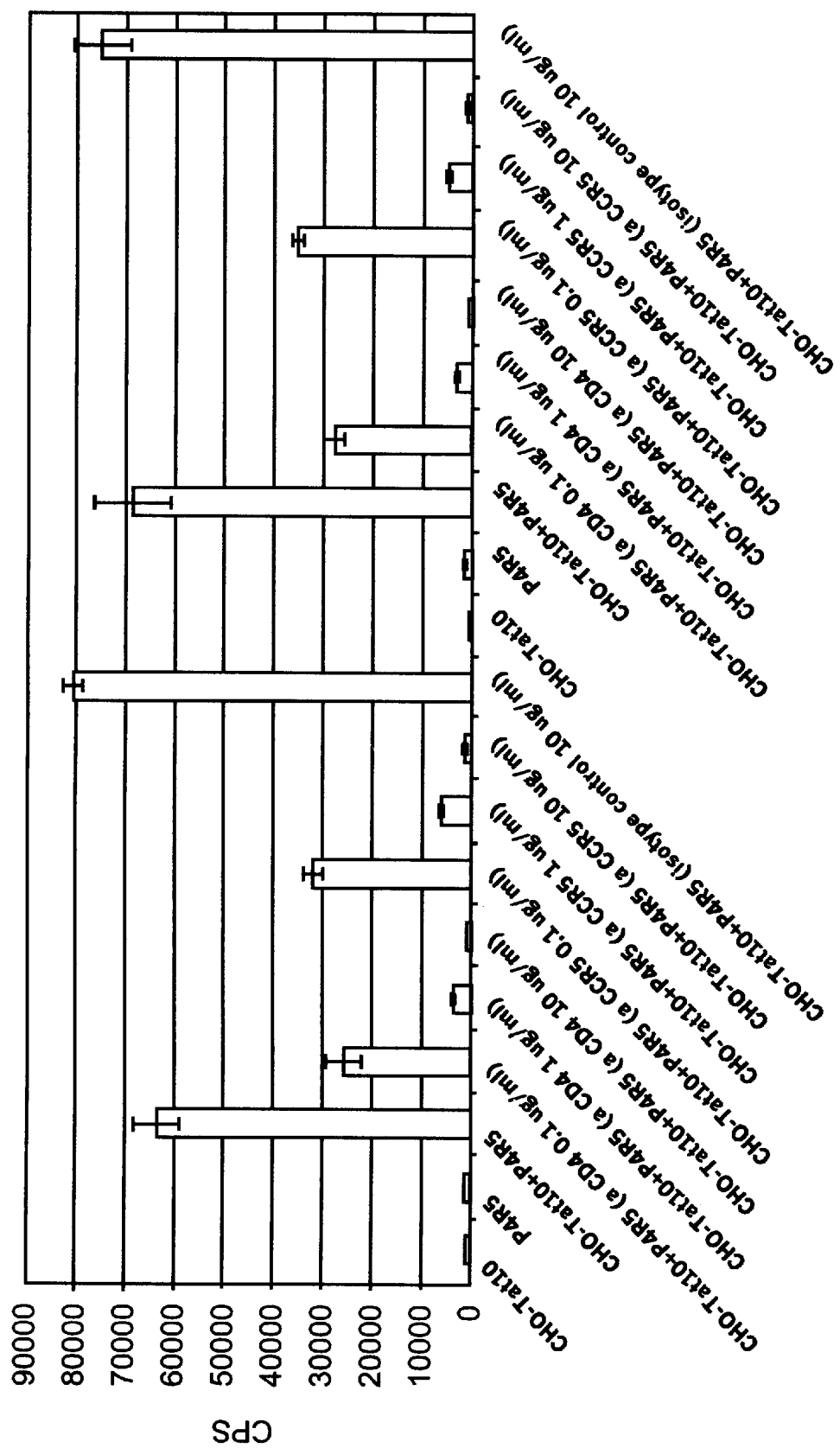
FIG. 1 provides a graphical depiction of the results of a cell fusion assay according to the subject invention performed with CHO-Tat10 cells (expressing JRFL envelope and Tat) and P4-CCR5 cells (expressing CD4, CCR5 and reporter gene). A strong luciferase signal was observed when these cells are mixed together. Inhibition was detected when the fusion was performed in the presence of monoclonal antibodies directed against CD4 (labeled "aCD4") or CCRF (labeled "a CCR5), but not isotype control antibody, at the indicated doses. Two different experiments are shown (Set 1 and Set 2).

Cell fusion assays (screening methods) for identifying antiviral compounds are provided. In the cell fusion assays of the subject invention, a first cell that stably expresses on its surface an envelope protein of an enveloped virion and a second cell that stably expresses on its surface a receptor for the viral envelope protein are employed. The first and second cells each contain one component of a two-component signal producing or reporter system, e.g., a Tat based reporter system, which system produces a detectable signal in the presence of cell fusion. In practicing the subject screening methods, the first and second cells are first contacted with each other under cell fusion conditions in the presence of a candidate inhibitory agent. Next, the presence or absence of the detectable signal is detected. Finally, the inhibitory activity of the candidate agent is derived from the presence or absence of the detectable signal. Also provided are high throughput embodiments of the subject methods. In addition to the subject methods, systems and kits for performing the subject methods are provided.

Before the subject invention is further disclosed and described, it is to be understood that this invention is not limited to particular components, devices or steps as such may, of course, vary. It is also to be understood that the terminology used herein is for the purpose of describing particular embodiments only, and is not intended to be limiting, since the scope of the present invention will be limited only by the appended claims.

In this specification and the appended claims, the singular forms "a," "an" and "the" include plural reference unless the context clearly dictates otherwise. Unless defined otherwise, all technical and scientific terms used herein have the same meaning as commonly understood to one of ordinary skill in the art to which this invention belongs.

The instant invention is shown and described herein in what is considered to be the most practical, and preferred embodiments. It is recognized, however, that departures may be made there from, which are within the scope of the invention, and that obvious modifications will occur to one skilled in the art upon reading this disclosure.

In further describing the present invention, the subject screening methods are described first in greater detail, followed by a review of the systems and kits for use in practicing the subject screening methods.

Screening Methods

As summarized above, the subject invention is directed to cell fusion assays useful for identifying antiviral compounds. In other words, the subject methods are directed to cell fusion assays that can be employed to identify compounds that inhibit viral activity. Antiviral compounds identified by the subject methods are compounds that inhibit receptor mediated entry of a viral particle into a target cell that displays the receptor on its surface. By inhibit is meant that they at least impede the receptor mediated entry of the virus into the target cell, where the compounds identified by the subject methods may substantially, if not completely, prevent receptor mediated entry of the virus into the target cell. As the subject assays are cell fusion assays, a first cell, i.e., the virion cell, and second cell, i.e., the target cell, are employed, where fusion of the cells or lack thereof in the presence of a candidate inhibitory agent is employed to characterize the antiviral activity of the candidate agent.

The first cell employed in the subject methods is the "virion" cell, by which is meant that it represents the virus particle for which the candidate agent is being assayed for inhibitory activity. The first cell is typically a eukaryotic cell, where the eukaryotic cell is a cell that can be grown in culture, typically using standard laboratory procedures and mediums well known to those of skill in the art. The first cell may be any cell that is not susceptible to toxic effects of chronically expressing viral envelope glycoproteins, that permit cell surface expression of such proteins, that can stably express HIV Tat without experiencing toxic effects, and that do not express complete receptors for such envelopes. A representative cell of interest for use as the first cell include is the Chinese hamster ovary (CHO) cell.

As the first cell represents the virion cell, it displays a protein found on the surface of the virion of interest, where the protein displayed on the surface of the cell participates in the entry mechanism of the virion that the first cell represents into the target cell. As the subject assays are generally directed to assays for antiviral compounds that are active with respect to enveloped viruses, the viral protein displayed or present on the surface of the first cell is a surface protein of an enveloped virus. By enveloped virus is meant a virus that is encapsulated by a lipid bilayer or surrounded by a lipid bilayer, where present on the surface of the encapsulating/surrounding/enveloping lipid bilayer is at least one type of surface protein, which may be a glycoprotein, where the surface protein participates in receptor mediated entry into the target cell of the enveloped virus. Proteins of interest that may be displayed on the surface of the first cell include surface proteins from a number of different types of enveloped viruses, including lentiviruses, e.g., HIV, influenza, vesicular stomatitis virus (VSV), filoviruses and the like. Specific proteins of interest that may be present on the surface of the first cell employed in the subject methods include, but are not limited to: a gp120/gp41 proteins (for assays to identify anti HIV compounds); and the like.

A feature of the present invention is that the viral surface protein displayed on the surface of the first cell is stably expressed in the cell, as opposed to the transiently expressed surface proteins found in vaccinia based cell fusion assays, as reviewed in Berger et al., HIV: A Practical Approach, J. Kam ed. IRL Press Vol. 2:123–145 (1995). By stably expressed is meant that the viral coat protein is not expressed in a transient manner. In general, the first cell comprises a coding sequence for the viral surface protein stably integrated into its genome in a manner such that it is expressed in the first cell and directed to the cell surface where it is displayed. Typically, the first cell genome has incorporated into its genome an expression construct that includes a suitable promoter operably linked to a coding sequence for the viral coat protein, where the expression construct is expressed in the first cell and the viral coat protein expression product is transported to the cell surface where it is displayed.

The first or "virion" cells employed in the subject methods can be prepared using standard molecular biology procedures known to those of skill in the art, where the particular protocol employed to make the first cell is not critical to the invention. A representative protocol for the preparation of a first or virion cell is described in the experimental section, infra.

The second cell of the subject methods represents the target cell, i.e., the cell that the virus of interest enters. Like the first cell, the second cell is typically a eukaryotic cell, where the eukaryotic cell is a cell that can be grown in culture, typically using standard laboratory procedures and mediums well known to those of skill in the art. The second cell may be any cell that can stably express the complete viral receptors and a reporter gene construct without toxic effects. Specific cell types of interest for use as the second or target cell include, but are not limited to: 293, HOS, HeLa and the like, where in many embodiments the cell is a 293 cell.

As the second cell represents the target cell, it displays a protein found on the surface of the target cell of interest, where the protein displayed on the surface of the cell participates in the entry mechanism of the virion that the first cell represents into the target cell. In many embodiments, the protein expressed on the surface of the target cell is one that is a cell surface receptor protein that is employed by the virus of interest for receptor mediated fusion entry. Specific receptor proteins of interest include, but are not limited to: hCD4, hCCR5, hCXCR4 (for assays to identify anti-HIV compounds); and the like.

Another feature of the present invention is that the receptor protein displayed on the surface of the second cell is stably expressed in the cell. In general, the second cell comprises a coding sequence for the receptor protein stably integrated into its genome in a manner such that it is expressed in the second cell and directed to the cell surface where it is displayed. Typically, the second cell includes an expression construct made up of a suitable promoter operably linked to the receptor coding sequence, where the expression construct is integrated into the second cell genome in a manner such that the receptor coding sequence is expressed and the expressed receptor protein is transported to the cell surface where it is displayed.

The second or "target" cells employed in the subject methods can be prepared using standard molecular biology procedures known to those of skill in the art, where the particular protocol employed to make the second cell is not critical to the invention. A representative protocol for preparation of the second cell is described in the experimental section, infra.

An important feature of the present invention is that the first and second cells each include one component of a two component signal producing system or reporter system that produces a detectable signal when the first and second cells are fused together but does not produce a detectable signal when no cell fusion takes place. As such, the first cell includes one component of the two component system, e.g., a transacting factor that turns on expression of a reporter gene construct, and the second cell includes the other component of the two component system, e.g., an expression construct that encodes a detectable product, which may be either directly or indirectly detectable, in response to contact with the trans acting factor of the first cell.

Where the two-component system is made up of a first trans acting factor and a second expression construct responsive thereto, the expression construct typically encodes a detectable product, which product may be directly or indirectly detectable. Examples of directly detectable products include chromogenic, including fluorescent proteins, e.g., fluorescent proteins such as green fluorescent proteins from Aquoria victoria, anthozoa derived fluorescent proteins, which proteins are known to those of skill in the art. Examples of indirectly detectable products include enzymes that produce a detectable signal in response to the presence of an appropriate substrate, where the detectable signal may be light, e.g., where a bioluminescent enzyme is employed, such as firefly luciferase. In alternative embodiments, the enzyme may convert a substrate into a directly detectable product, e.g., a chromogenic, including fluorescent product. Examples of this latter embodiment include the E. coli β-gal (beta-galactosidase) enzyme, and the like.

In many embodiments, the two component system includes a trans acting factor responsive expression construct that encode as enzyme that converts a substrate into a detectable product, where the detectable product is a chromogenic product, where in preferred embodiments the detectable product is a fluorescent product. In this embodiment, the system employed in the subject invention typically produces an enzyme in the presence of cell fusion that converts a substrate to detectable product, such as a chromogenic and preferably a fluorescent product. This enzyme is produced only in the presence of cell fusion by having a trans acting factor in the first cell which acts on a promoter of an enzyme expression cassette in the second cell such that when cell fusion occurs, the trans acting factor binds to the promoter of the expression cassette causing expression of the enzyme which is then present to convert a substrate to a detectable product, e.g., a fluorescent product.

In many preferred embodiments, the two component system is a Tat reporter system, which is made up of an HIV Tat protein present in one of the first or second cell and HIV LTR-reporter enzyme construct in the other of the first or second cell. When the first and second cells fuse, the Tat protein binds to the Tat responsive LTR of the expression construct or cassette to drive expression of the operably linked enzyme, which in turn converts the substrate to the detectable product. The LTR may be operably linked to a number of different enzyme coding sequences, where coding sequences of interest include, but are not limited to: β-gal, luciferase and the like.

In practicing the subject screening methods, the first and second cells as described above are first contacted with each other under cell fusion conditions in the presence of a candidate inhibitory agent. By cell fusion conditions is meant conditions in which the first and second cells fuse with each other in the absence of inhibitory agents that prevents cell fusion. In other words, cell fusion conditions are conditions that permit fusion of the first and second cell when contacted with each other in the absence of an agent that inhibits fusion mediated by interaction of the viral surface protein of the first cell and the receptor on the surface of the second cell. Cell fusion conditions are typically conditions that mimic a physiological environment, where the pH typically ranges from about 5 to 8, usually from about 6 to 8, where the pH is normally around 7 and the temperature typically ranges from about 30 to 40, usually from about 35 to 38 and more usually about 36 to 38, e.g., 37° C. Generally, contact occurs in a physiologically acceptable aqueous buffer medium, where suitable mediums include, but are not limited to: TEN buffer, HEPES-buffered culture medium, and the like. Representative cell fusion conditions that are suitable for use in the subject assay methods are provided in the experimental section, infra.

The first and second cells, i.e., the virion and target cells, respectively, are contacted using any convenient protocol, where typically the first and second cells are placed into a container that can hold a volume of a fluid medium, e.g., a well or analogous structure. The contact protocol produces a reaction volume of an aqueous fluid medium that includes both first and second cells. The total number of cells present in the reaction volume typically ranges from about 5,000 to 50,000 cells. The reaction volume typically ranges from about 25 to 200 microliters.

As mentioned above, the first and second cells are contacted with each other in the presence of a candidate inhibitory agent. The candidate inhibitory agent may be present in one of the first or second cell compositions prior to production of the reaction volume or added to the reaction volume following its production, as described above. Alternatively, the candidate agent may be present in the fluid container into which the first and second cell compositions are placed to produce the reaction volume. The manner in which the first and second cell populations are combined with the candidate inhibitory agent is not critical, so long as the candidate inhibitory agent is present to prevent fusion of the first and second cells if it has inhibitory activity.

A variety of different candidate inhibitory agents may be screened for antiviral activity using the subject methods. Candidate agents encompass numerous chemical classes. In certain embodiments, they are organic molecules, preferably small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof. Candidate agents of interest also include peptide and protein agents, such as antibodies or binding fragments or mimetics thereof, e.g., Fv, F(ab')$_2$ and Fab.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

The amount of candidate agent that is present in the reaction mixture may vary, particularly depending on the nature of the candidate agent. Where the agent is a small organic molecule, the amount of agent present in the reaction mixture typically ranges from about 1 nanomolar to 1 micromolar in many embodiments. Where the agent is an antibody or binding fragment thereof, the amount of the agent typically ranges from about 1 nanomolar to 1 micromolar in many embodiments. The amount of any particular agent to include in a given reaction volume can be readily determined empirically using methods known to those of skill in the art.

Contact of the first and second cell in the presence of the candidate agent is maintained for an incubation period. Where desired, the cells of the reaction volume may be agitated to ensure adequate mixing and presentation of viral coat protein to cell surface receptor.

At the end of the incubation period, the reaction mixture is lysed to produce a cell lysate mixture. Lysing of the cells of the reaction mixture may be accomplished using any convenient protocol. In many embodiments, the cells are contacted with an effective amount of a detergent, where representative detergents include those employed in the working exemplification infra. The amount of detergent employed will vary depending on the particular detergent used and can be readily determined empirically by those of skill in the art. Following contact of the reaction mixture with the lysing agent, the reaction mixture is maintained for a period of time sufficient for cell lysis to occur, at the end of which time a cell lysate is produced.

While the above step has been described in terms of contacting the first and second cells with a single candidate agent, in certain embodiments the cells may be contacted with two or more candidate agents, e.g., where the potential antiviral activity of two or more agents together is screened with the subject assays.

The next step in the subject cell fusion assays is to detect the signal of the signal producing system. Where the signal producing system produces a directly detectable product, e.g., where the expression construct encode a fluorescent protein, detection merely includes detecting the product. The particular detection protocol employed necessarily varies depending on the nature of the directly detectable product. For example, where the directly detectable product is a fluorescent protein, the lysate is irradiated with light of an appropriate wavelength to excite the fluorescent protein and emission from the fluorescent protein is detected.

In those embodiments where the signal producing system produces an enzyme that converts a substrate to a detectable product, the detection step typically first requires contacting the cell lysate with a substrate for the reporter enzyme. The substrate may be contacted with the lysate using any convenient protocol, e.g., by placing the lysate into a container having the substrate, by introducing the substrate into the lysate, etc. The nature of the particular substrate necessarily depends on the nature of the reporter enzyme which is present in the two component, e.g., Tat, reporter system of the subject assays. In many embodiments, the substrate is one that is converted by the reporter enzyme into a chromogenic product. Of interest in certain embodiments are substrates that are converted by the enzyme into a fluorescent product. Representative substrates include, but are not limited to: Galacton substrate and the like. The amount of substrate that is contacted with the lysate may vary, but typically ranges from about 1 nanomolar to 1 micromolar.

Following another incubation period, the presence or absence of detectable product in the lysate is detected. In other words, the lysate is evaluated for the presence or absence of detectable product. The lysate is evaluated following a predetermined incubation period, where this incubation period typically ranges from about 1 minute to 2 hours. The particular detection protocol employed varies depending on the nature of the detectable product. For example, where the detectable product is a fluorescent product, the detection protocol employs the use of a fluorescent light detection means, e.g., a fluorescent light scanner, which can scan the lysate for the presence of fluorescent signal.

The presence or absence of detectable signal from the signal producing system, e.g., detectable product in the lysate, is then used to derive information as to whether cell fusion occurred and, therefore, the inhibitory activity of the candidate agent tested in the cell fusion assay. The presence of a signal in the lysate is indicative of cell fusion, and therefore a lack of inhibitory activity by the candidate antiviral agent. In other words, presence of signal indicates a lack of inhibitory activity by the candidate agent since signal is only present when cell fusion occurs. As such, absence of signal indicates that the candidate agent possesses antiviral activity.

The signal can be correlated to the antiviral activity of the candidate agent in either a qualitative or quantitative manner. As such, the presence of any amount of signal can be used to determine that the candidate lacks sufficient antiviral activity where the absence of signal can be used as indication of sufficient antiviral activity. One can also employ a threshold value, whereby any signal above the threshold value represents insufficient activity and any signal below the threshold value represents sufficient activity. One can also evaluate the signal in at least a semi-quantitative manner, in which the amount of signal detected is used as a direct indication of the level of antiviral activity, which approach is based on the assumption that the amount of signal detected is proportional to the amount of antiviral activity of the compound. In this evaluation protocol, a smaller amount of signal indicates a greater amount of antiviral activity, such that the amount of signal has an inverse relationship with the amount of antiviral activity of the candidate agent.

The above signal evaluation and antiviral activity derivation step may be accomplished using any convenient means. Thus, the signal may be subjectively evaluated to determine the antiviral activity of the test compound. This subjective evaluation may involve comparing the signal to a set of control signals. While the evaluation may be done manually, of interest in many embodiments is the use of a computing or data processing means that compares the detected signal with a set of control values to automatically provide a value for the antiviral activity of the test compound.

The above described cell fusion protocol provides an efficient and rapid means for evaluating the antiviral activity of a candidate compound. The above cell fusion assays can be performed in a short period of time, where the typical time required to perform the assay typically ranges from about 1 hour to 18 hours.

The above cell fusion protocols are amenable to high throughput formats, by which is meant that the above cell fusion assays can be performed in an automated fashion to screen a plurality of different candidate agents simultaneously. As such, large numbers of compounds can be screened using automated means at substantially the same time. By large numbers is meant at least about 10,000 to 1,000,000. In these high throughput formats, one or more of the above steps, including all of the steps, may be automated, including cell /candidate agent contact, lysate production, signal detection and signal evaluation.

Systems

Also provided are systems for practicing the above described fusion systems. The subject systems at least include a first cell and a second cell as described above. The subject systems may also include a substrate that gives rise to a detectable product in the presence of cell fusion, e.g., where the cell fusion reporter system of the first and second cell produces an enyzme upon cell fusion that converts a substrate into a detectable product. Representative substrates include, but are not limited to, the substrates described above. In addition, the substrates may include one or more additional components that find use in practicing the subject cell fusion assays, where additional components of interest include, but are not limited to, buffer mediums, and the like.

Kits

Also provided are kits for use in practicing the above described fusion systems. The subject kits at least include a first cell and a second cell as described above, or one or more precursors thereof. Precursors of interest include components that can be employed to produce the first and second cells, e.g., eukaryotic cell lines, such as CHO cells, 293 cells and the like, vectors for transforming eukaryotic cells to express the receptor or viral envelope protein on the surface, e.g., plasmids capable of genome integration and subsequent expression of the surface protein, etc. The subject kits may also include a substrate that gives rise to a detectable product in the presence of cell fusion, e.g., where is the cell fusion reporter system of the first and second cell produces an enzyme upon cell fusion that converts a substrate into a detectable product. Representative substrates include, but are not limited to, the substrates described above. In addition, the kits may include one or more additional components that find use in practicing the subject cell fusion assays, where additional components of interest include, but are not limited to, buffer mediums, lysis buffer and the like.

The above described kit components are typically present in separate containers, e.g., wells, vials etc., which provides for storage stability until use. The subject kits also typically include instructions for practicing the subject cell fusion assays. Finally, the kits include instructions for practicing the subject cell fusion assay methods, where such instructions may be present on one or more of the kit components, the kit packaging and/or a kit package insert.

The following examples are offered by way of illustration and not by way of limitation.

EXPERIMENTAL

I. Representative Cell Fusion Assay

The following assay is based on the finding that HIV-1 Tat expression in CHO-JRFL cells drives expression of a β-gal construct (under HIV-1 LTR regulation) upon fusion with CD4/CCR5-bearing cells carrying this Tat-dependent expression construct. CHO-JRFL cells (produced by Lipofectamine-mediated stable co-transfection of CHO cells with expression plasmids encoding the HIV-1 JRFL envelope glycoproteins (pcDNA3-JRFL) and Rev (pRevHygro), growth selection in G418 and Hygromycin, and screening by immunoblotting for expression) were transiently transfected with a Tat expression construct (pEV280, as described in Ott et al. Science 295: 1481–1484, 1997) and then mixed with "GHOST" cells expressing CD4/CCR5 and carrying an HIV-1 LTR GFP expression construct (Morner et al. J Virology 73:2343–9, 1999). Cell-cell hybrids formed in these mixtures were readily detectable as intensely fluorescent syncytia under fluorescence microscopy with very little background autofluorescence.

Next, the GHOST cells were replaced with P4-CCR5 cells which carry the desired LTR-driven, Tat-dependent β-gal construct (produced by Ned Landau and described in the catalogue of the NIH AIDS Research Reference and Reagent Program) and readily detected blue syncytia following X-Gal staining. Based on these data, a stable CHO-JRFL derivative expressing Tat was developed. To accomplish this task, Tat cDNA (obtained from Eric Verdin) was subcloned from pEV280 into an expression plasmid (pCMV4puro, prepared by modifying pCMV4delta, obtained from Mark Feinberg) carrying an appropriate selectable antibiotic resistance marker (puromycin), and then stably transfected CHO-JRFL cells were selected. 12 resistant colonies were then screened by fusion with P4-CCR5 cells and X-Gal color development. This work led to the identification of 8 positive clones, one of which was expanded and studied in further detail.

A more complete experiment, including negative controls, verified that this clone (CHO-Tat10) indeed generated intense blue staining upon fusion to P4-CCR5 cells, and that the background color level was extremely low. In addition, a neutralizing anti-CD4 antibody (obtained from BD Pharmingen) was used as further validation. This antibody caused potent, dose-dependent inhibition of both syncytium formation and blue color development.

Finally, an experiment was performed with the anti-CCR5 antibody 2D7 (obtained from BD Pharmingen), which caused dramatic suppression of fusion with dose-response curves that are very similar to those obtained with anti-CD4. These findings confirm that the cell-cell fusion we observe in this assay is CD4- and CCR5-dependent, and that it can be neutralized effectively by known inhibitors.

The above results indicate the successful development of a cell fusion assay system for gp120- and CD4/CCR5-dependent cell-cell fusion. This new assay is based exclusively on stable transfectant cell lines, is simple and relatively rapid, and appears to have a good dynamic range based at this stage on visual inspection.

II. Representative Fusion/β-Gal Assay

The protocol described below (III. High Throughput Adaptable Quantitative Cell-Cell Fusion/β-GAL Assay Protocol) was used to test receptor- and envelope-mediated cell-cell fusion. CHO-Tat10 cells were cultured alone or with P4-CCR5 cells (labelled here as P4R5) in the absence or presence of anti-CD4 (obtained from BD Pharmingen) or anti-CCR5 (2D7, obtained from BD Pharmingen) monoclonal antibodies at the indicated concentrations, for 18 hours. At termination, cells were lysed and signal was detected as described below with Galacto-Light and Tri-lux Luminometer. Two experiments (Set 1 and Set 2) were performed in parallel, each condition with triplicate samples within each sety. Error bars are S.E.M.

III. High Throughput Adaptable Quantitative Cell-Cell Fusion/β-GAL Assay Protocol A. Materials CHO-Tat cell line: constitutively expressing HIV-1 JRFLenv and HIV-1 Tat. P4-CCR5 cell line: expressing hCD4, hCCR5 and containing LTR-betagal construct (as described in (Charneau et al., J. Mol. Biol. (1994) 241:651–662). This cell line was produced by Ned Landau and is described in the NIH AIDS Research Reference and Reagent catalogue. TEN buffer: 40 mM Tris pH7.4, 1 mM EDTA pH8.0 and 150 mM NaCl Galacto-Light™ Kit: Tropix, Catalog # BL100G Tri-lux Luminometer: Wallac, model 1450 microbeta B. Method 1. Plating of Cells
   1). Detach CHO-Tat and P4-CCR5 cells with TEN buffer (enough to cover cells) at room temperature for 5 min. Dilute TEN with 1 vol. of culture media.
   2) Count cells, then pellet.
   3) Resuspend each set of cells in the media of mixed RPMI1640 and DMEM (1:1 ratio) to a concentration of $0.8 \times 10^6$ cells/ml.
   4) Plate a total of 50 µl ($0.04 \times 10^6$) cells per well (25 µl of each cell line).

5) Add 50 µl mixed media (for control samples) or inhibitors to total volume of 100 µl/well, mix gently by pipetting.
6) Incubate at 37° C. overnight (18 hours)

2. Lysis of Cells
   1) Pour out media.
   2) Rinse cell cultures once with PBS (pour out PBS and invert plate onto a paper towel to dry).
   3) Add 25 µl of Lysis Solution with 0.5 mM DTT to each well and incubate at RT for 10 min.
   4) Lightly rock the plate to mix the lysates.

3. Detection of Signals
   1) Dilute Galacton substrate 1:100 with Reaction Buffer Diluent to make Reaction Buffer.
   2) Equilibrate Reaction Buffer and Accelerator to room temperature.
   3) Add 15 µl of Lysis Solution to microplate wells.
   4) Transfer 5 µl of lysate to the above microplate wells, to total volume of 20 µl/sample.
   5) Add 70 µl of Reaction Buffer and mix, cover the plate with foil and incubate at room temperature for 60 min.
   6) Place plate in luminometer. Inject 100 µl of Accelerator. After a 1 sec delay, read the signal for 5 sec/well.

It is evident from the above results and discussion that an improved cell fusion assay for identifying antiviral compounds is provided. An important improvement provided by the subject invention is that vaccinia based expression is not required, which allows one to avoid viral based expression and its inherent disadvantages. In addition, the subject assay is readily amenable to high throughput format, which makes it particularly suited for screening large libraries of potential pharmaceutical compounds. As such, the subject invention represents a significant contribution to the art.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A method of assaying whether a candidate agent inhibits CD4/CCR5-mediated fusion of a human immunodeficiency virus (HIV) virion and its target cell, said method comprising:
   (a) combining under cell fusion conditions said candidate agent with:
      (i) a first eukaryotic cell that stably displays an envelope protein of said HIV virion on its surface; and
      (ii) a second eukaryotic cell that stably displays both a CD4 receptor and a CCR5 receptor of said target cell for said envelope protein on its surface;
      wherein said first and second cells further comprise a stably-expressed two component signal producing system that provides a detectable signal upon fusion of said first and second cells;
   (b) identifying the presence or absence of said detectable signal; and
   (c) deriving the inhibitory activity of said candidate agent from the presence or absence of said detectable signal, wherein inhibitory activity indicates that the candidate agent inhibits CD4/CCD5-mediated fusion of and HIV virion and its target cell.

2. The method according to claim 1, wherein said first cell comprises a coding sequence for said envelope protein integrated into its genome.

3. The method according to claim 1, wherein said second cell comprises a coding sequence for said target cell receptor integrated into its genome.

4. The method according to claim 1, wherein said first cell is a Chinese hamster ovary cell.

5. The method according to claim 1, wherein said two component signal producing system comprises a Tat protein and a Tat responsive expression construct that codes for a reporter enzyme.

6. The method according to claim 5, wherein said identifying step (b) comprises:
   (i) lysing said contacted cells;
   (ii) contacting said lysed cells with substrate that is converted by said reporter enzyme into a detectable product if cell fusion has occurred;
   (iii) detecting the presence or absence of said detectable product.

7. The method according to claim 6, wherein the amount of detectable product produced in step (ii) is proportional to the amount of cell fusion that occurs in the assay.

8. The method according to claim 6, wherein said detectable product is a chromogenic product.

9. The method according to claim 8, wherein said chromogenic product is a fluorescent product.

10. The method according to claim 1, wherein said method is a high throughput screening method that simultaneously assays a plurality of candidate inhibitory agents for cell fusion inhibitory activity.

11. A method of assaying whether a candidate agent inhibits CD4/CR5-mediated fusion of a human immunodeficiency virus (HIV) virion and its target cell, said method comprising:
   (a) combining under cell fusion conditions said candidate agent with:
      (i) a Chinese hamster ovary cell having a coding sequence for an envelope protein of said HIV virion stably integrated into its genome and that stably displays an envelope protein of said enveloped virion on its surface; and
      (ii) a second eukaryotic cell having a coding sequence for both a CD4 receptor and a CCR5 receptor of said target cell for said envelope protein integrated into its genome and that stably displays said receptors on its surface;
      wherein said first and second cells further comprise a Tat reporter system that provides a detectable fluorescent signal upon fusion of said first and second cells;
   (b) identifying the presence or absence of said fluorescent detectable signal by:
      (i) lysing said contacted cells;
      (ii) contacting said lysed cells with substrate that is converted into a fluorescent detectable product if cell fusion has occurred; and
      (iii) detecting the presence or absence of said detectable product; and
   (c) deriving the inhibitory activity of said candidate agent from the presence or absence of said detectable fluorescent signal, wherein inhibitory activity indicates that the candidate agent inhibits CD4/CCD5-mediated fusion of and HIV virion and its target cell.

12. The method according to claim 11, wherein said Tat reporter system is made up of a Tat coding sequence in said first cell and a Tat inducible coding sequence in said second cell.

13. The method according to claim 11, wherein the amount of detectable product produced in step (b)(ii) is proportional to the amount of cell fusion that occurs in the assay.

14. The method according to claim 11, wherein said method is a high throughput screening method that simultaneously assays a plurality of candidate inhibitory agents for cell fusion inhibitory activity.

15. A system for use in the method of claim 1, said system comprising:
   (a) a first eukaryotic cell that stably displays an envelope protein of said HIV virion on its surface; and
   (b) a second eukaryotic cell that stably displays both a CD4 receptor and a CCR5 receptor for said envelope protein on its surface;
   wherein said first and second cells further comprise a Tat reporter system that provides a detectable signal upon fusion of said first and second cells.

16. A kit for use in the method of claim 1, said system comprising:
   (a) a first eukaryotic cell that stably displays an envelope protein of said HIV virion on its surface; and
   (b) a second eukaryotic cell that stably displays both a CD4 receptor and a CCR5 receptor for said envelope protein on its surface;
   wherein said first and second cells further comprise a stably expressed Tat reporter system that provides a detectable signal upon fusion of said first and second cells.

* * * * *

UNITED STATES PATENT AND TRADEMARK OFFICE
CERTIFICATE OF CORRECTION

PATENT NO. : 6,451,598 B1
APPLICATION NO. : 09/779324
DATED : September 17, 2002
INVENTOR(S) : Mark A. Goldsmith It is certified that error appears in the above-identified patent and that said Letters Patent is hereby corrected as shown below:

Please add the Statement Regarding Federally Sponsored Research beginning on column 1, line 12, with the following statement:

STATEMENT REGARDING FEDERALLY SPONSORED RESEARCH
--This invention was made with government support under grant no. DK009171 awarded by the National Institutes of Health. The government has certain rights in this invention.--

Signed and Sealed this

Seventeenth Day of August, 2010

David J. Kappos
*Director of the United States Patent and Trademark Office*